United States Patent [19]

Lukes et al.

[11] Patent Number: 5,756,792
[45] Date of Patent: May 26, 1998

US005756792A

[54] DIRECT REACTION OF PHOSPHORUS ACIDS WITH THE HYDROXY GROUP ON THE SURFACE OF SOLIDS

[75] Inventors: Ivan Lukes, Prague, Czech Rep.; Louis DuBose Quin, Amherst, Mass.

[73] Assignee: University of Massachusetts, Boston, Mass.

[21] Appl. No.: 290,334

[22] Filed: Aug. 15, 1994

[51] Int. Cl.$^6$ .................................................. C07F 7/08
[52] U.S. Cl. .......................... 556/405; 556/400; 423/701
[58] Field of Search ............................ 556/400, 405; 423/701

[56] References Cited

U.S. PATENT DOCUMENTS

| | | | |
|---|---|---|---|
| 5,334,741 | 8/1994 | Quin et al. | 558/110 |
| 5,374,755 | 12/1994 | Neue et al. | 556/400 |
| 5,449,736 | 9/1995 | Cabasso et al. | 556/405 X |

OTHER PUBLICATIONS

*American Chemical Society*, "Direct Reaction of Phosphorus Acids with Hydroxy of a Silanol and on the Silica Gel Surface", pp. 1737–1741 (1994).

*Xth International Symposium on Organosilicon Chemistry* (*Abstracts of Lectures and Oral & Poster Contributions*). "The Direct Reaction of Phosphorus Acids with Hydroxy of a Silanol and on the Silica Gel Surface," p. 213 (1993).

Voronkov, M. G., *Heterolytic Cleavage Reactions of the Siloxane Bond*, Soviet Scientific Reviews, Section B, vol. 15, Part 1 (Apr., 1990).

*Primary Examiner*—Paul F. Shaver

[57] ABSTRACT

The subject invention encompasses a method for producing phosphorus acid ester derivatives of silicon-hydroxy groups found on the surface of solid silica gel or zeolites.

11 Claims, No Drawings

DIRECT REACTION OF PHOSPHORUS ACIDS WITH THE HYDROXY GROUP ON THE SURFACE OF SOLIDS

BACKGROUND OF THE INVENTION

Silica gel and zeolites are commonly known and have a wide variety of commercial applications in industrial, scientific and health care fields. Modification of silica gel and zeolites could have considerable impact on the value of these compounds in the above-mentioned fields. One such modification involves the phosphorylation of silica gel or zeolites. Previously, the direct attachment of organophosphorus acid residues to surface OH groups of solid silica gel or zeolites has been accomplished by the action of highly reactive, low coordination intermediates, as disclosed in U.S. Pat. No. 5,334,741 to Quin et al., issued Aug. 2, 1994. Alkyl metaphosphates represent one type of low coordination intermediate that have been employed. It has now been discovered that generating such low coordination intermediates is not necessary to accomplish the derivatization of the solid surface. It has been found that organophosphorus acids will react directly with surface OH groups of silica gel and zeolites to form organophosphorus acid ester derivatives of silica gel or zeolites. This direct method is much simpler and less expensive than methods requiring preparation of substances capable of generating reactive, low coordination intermediates.

Therefore, it is an object of the present invention to provide a method for producing phosphorus acid ester derivatives of silicon-hydroxy groups found on the surface of silica gel or zeolites. It is a further object of the invention to produce these derivatives directly without the action of reactive, low coordination intermediates such as alkyl metaphosphates.

These and other objects of the present invention will become readily apparent from the detailed description which follows.

SUMMARY OF THE INVENTION

The present invention relates to a method for producing phosphorus acid ester derivatives of silicon-hydroxy groups found on the surface of silica gel or zeolites comprising the steps of a) creating a suspension of silica gel or zeolites in an inert solvent using an amount of from about 5 ml of inert solvent/g of silica gel or zeolites to about 100 ml of inert solvent/g of silica gel or zeolites, wherein free hydroxy groups are present in the silica gel or zeolites; b) treating the suspension with an organophosphorus acid to create a mixture using a ratio of organophosphorus acid molecules to free hydroxy groups in the silica gel or zeolites of from about 0.01:1 to about 100:1; c) heating the mixture for from about 5 minutes to about 2 hours at reflux of the inert solvent; d) filtering the mixture to create a solid; e) washing the solid in inert solvent of the same type used in step (a).

DETAILED DESCRIPTION OF THE INVENTION

The method of the present invention for producing phosphorus acid ester derivatives of silicon-hydroxy groups found on the surface of silica gel or zeolites comprises the steps of suspending solid silica gel or zeolites in an inert solvent, treating the suspension with an organophosphorus acid to create a mixture, heating the mixture, filtering the mixture to create a solid, and washing the solid with inert solvent. The present method also comprises reacting the mixture for about 1 to about 4 hours at about 25° C., rather than heating the mixture. Most preferred for use in the present method is silica gel that is suitable for human administration.

The following terms will be designated as follows: "g" for gram, and "ml" for milliliter. A detailed description of essential and optional components and conditions of the present method is given below.

Solid Silica Gel and Zeolites

The present method utilizes silica gel and zeolites. Silica gel is a regenerative adsorbent consisting of amorphous silica which is derived from sodium silicate and sulfuric acid. *Hawley's Condensed Chemical Dictionary*, Twelfth Edition, 1993. Silica gel is available in various grades. Most preferred for use in the present method is silica gel that is suitable for human administration. The term "suitable for human administration", as used herein, means a material that may be used by humans which provides the desired benefit without undue adverse side effects (such as toxicity, irritation or allergic response), and that is recognized in the industry as safe for topical or oral use by humans.

Zeolites are also known as $2/n\ M^{+n}O.Al_2O_3.ySiO_2.wH_2O$, wherein M represents a proton or a group IA or IIA element such as sodium, calcium, or magnesium, n is the cation valence, y is 2 or greater, and w is the number of water molecules contained in the interconnected voids or channels within the zeolite. *The Merck Index*, Tenth Edition, No. 9922, 1983. In the present method, M represents from about 0.1% to about 100% protons, and preferably from about 1% to 100% protons. Zeolites may be natural or synthetic. Synthetic zeolites are made either by a clay process (kaolin) or a gel process (sodium silicate and alumina), which form a matrix to which the zeolite is added. *Hawley's Condensed Chemical Dictionary*, Twelfth Edition, 1993.

Inert Solvent

In the present method, silica gel or zeolites are suspended in an inert solvent. The choice of inert solvent will largely depend on the organophosphorus acid utilized. Suitable inert solvents must effectively solubilize the organophosphorus acid and be non-reactive to the acid and silica gel or zeolites. Typical inert solvents useful in the present method include hexane, toluene, benzene, chlorobenzene, 2-propanol, 1–2, dichloroethane, and acetonitrile. Preferred are chlorobenzene, toluene, and hexane.

Organophosphorus Acid

The method of the present invention also utilizes organophosphorus acids. Suitable organophosphorus acids form ester linkages on reaction with silica gel and zeolites in an inert solvent. Typical organophosphorus acids useful in the present method include any alkyl and aryl phosphonic, phosphoric, phosphinic acids, and mixed acid ester compounds of phosphonic and phosphoric acids (i.e. dialkyl, diaryl, or alkylaryl phosphonic and phosphoric acids). Preferred are methyl- and phenylphosphonic acid, diphenylphosphinic acid, phenylphosphinic acid, and ethyl phosphoric acid. Most preferred are menthyl-, thymyl-, eugenyl-, vanillyl-, triclosanyl-, and dimenthyl-phosphoric acids.

Quantity of Reactants

In the present method, silica gel or zeolites (referred to together as "solids") are suspended in an inert solvent and then reacted with an organophosphorus acid. The amount of solvent needed may vary depending on the solubility of the acid, i.e. a more insoluble acid will require a greater amount of inert solvent/g of silica gel or zeolites. In general, the amount of inert solvent used is from about 5 ml inert solvent/g of solids to about 100 ml inert solvent/g of solids.

and preferably from about 10 ml inert solvent/g of solids to about 50 ml inert solvent/g of solids.

The amount of organophosphorus acid used in the present method is determined by the free hydroxy group content of the silica gel or zeolites. The term "free hydroxy group", as used herein, refers to a single OH group on the surface of the solids which is accessible for reaction with the organophosphorus acid. Free hydroxy group content of silica gel or zeolites will vary depending on the particular type of silica gel or zeolite used and may be determined by any method known in the art. A method for determining free hydroxy group content is described in Greenberg, *Journal of Physical Chemistry*, vol. 60, p. 325 (1956), which is incorporated herein by reference.

The amount of organophosphorus acid useful in the present method is expressed by a ratio of organophosphorus acid molecules to free hydroxy groups in the silica or zeolites. This ratio may be a simple 1:1 ratio or adjusted to achieve various desired end products and percentages of reacted hydroxy groups. For example, a several-fold molar excess of the acid relative to the hydroxy group content of the silica gel or zeolites used will ensure greater saturation of the free hydroxy groups. In general, the present method employs a ratio of molecules of organophosphorus acid to free hydroxy groups in the silica gel or zeolites of from about 0.01:1 to about 100:1, preferably from about 0.1:1 to about 50:1, and most preferably from about 0.5:1 to about 10:1.

Conditions

In the present method, the organophosphorus acid may be reacted from about room temperature (hereinafter referred to as "25° C.") to about the boiling point temperature, (also referred to as "at reflux"), of the inert solvent. Generally, the boiling point of the inert solvent controls the rate of the reaction, i.e. the higher the boiling point of the inert solvent, the shorter the reaction time. Therefore, depending on the boiling point of the inert solvent, the reaction time may vary from about 5 minutes to about 2 hours at reflux of the inert solvent, preferably from about 15 minutes to about 1.5 hours at reflux of the inert solvent; and from about 1 hour to about 4 hours at 25° C., preferably from about 1.5 hours to 3 hours at 25° C.

Organophosphoric acids used in the method described can alternatively be pre-formed in situ by the reaction of an alcohol with phosphoric acid anhydride. In this variation, phosphoric acid anhydride, or $P_2O_5$, is combined with an alcohol, such as ethanol or a solution of an alcohol and an inert solvent. Then either silica gel or zeolite is added. The alcohol can be used as the reaction solvent (or dissolved in an inert solvent) in a stoichiometric proportion relative to the quantity of $P_2O_5$ used or an amount in excess of that proportion. In the case of a stoichiometric reaction, the $P_2O_5$ to alcohol molar ratio is about 1:3. When the alcohol is used in excess, the $P_2O_5$ to alcohol ratio can vary anywhere from about 1:3 to about 1:300 and preferably from about 1:3 to about 1:30. In the latter case, any of the aforementioned inert solvents, except for 2-propanol or acetonitrile, can be used as the reaction inert solvent.

The phosphorus acid ester derivatives formed by the present method or the variation described may be recovered by simple filtration. Subsequently, the recovered product may be washed with fresh inert solvent which is of the same type used in the reaction. The recovered product may be air dried at this point or washed again with a solvent which is effective in removing any unreacted organophosphorus acid from the silica gel or zeolites due to the solvent's ability to solubilize the organophosphorus acid used. Therefore, the choice of solvent will depend on the solubility of the organophosphorus acid used in the reaction. Typical solvents include methylene chloride, and any alcohol with a molecular weight equal to or greater than ethyl alcohol. Preferred are 2-propanol, methylene chloride, and ethyl alcohol.

The following non-limiting examples illustrate embodiments of the present invention. The examples are given solely for the purpose of illustration and are not to be construed as limiting the scope of the invention.

EXAMPLE I

A solution of 2 g of phenylphosphonic acid in 40 ml of chlorobenzene containing 5 g of suspended silica gel is heated at reflux for 2 hours. The solid is recovered and washed with two 20 ml portions of 2-propanol. The solid is air-dried. This process yields silica gel containing phenylphosphonic acid groups directly attached to the silica gel surface via ester linkages. The formation of Si—O—P bonds are confirmed by $^{29}$Si and 31P CP-MAS NMR spectroscopy.

EXAMPLE II

A solution of 2 g of monomenthyl phosphoric acid in 100 ml of toluene containing 5 g of silica gel in suspension is heated at 90° C. for 3 hours. The mixture is filtered and the recovered solid is washed with 2-propanol. The solid is then air-dried. The dried solid has a $^{13}$P CP-MAS NMR signal at δ11. The process yields monomenthyl phosphoric acid directly attached to the surface of silica gel via an ester linkage.

EXAMPLE III

To a solution of 1 g of $P_2O_5$ in 50 ml of ethanol is suspended 5 g of suspended silica gel. The suspension is heated at reflux for 2 hours and the solid is recovered by filtration. After washing the solid with two 20 ml portions of ethanol, the solid is then air-dried. This process yields ethyl and diethyl phosphoric acids directly attached to the surface of silica gel via ester linkages. The formation of Si—O—P bonds are confirmed by $^{29}$Si and $^3$P CP-MAS NMR spectroscopy.

What is claimed is:

1. A method for producing phosphorus acid ester derivatives of silicon-hydroxy groups found on the surface of solid silica gel or zeolites comprising the steps of:
   a) creating a suspension of silica gel or zeolites in an inert solvent using an amount of from about 5 ml of inert solvent/g of silica gel or zeolites to about 100 ml of inert solvent/g of silica gel or zeolites, wherein free hydroxy groups are present in the silica gel or zeolites;
   b) treating the suspension with an organophosphorus acid to create a mixture using a ratio of organophosphorus acid molecules to free hydroxy groups in the silica gel or zeolites of from about 0.01:1 to about 100:1;
   c) heating the mixture for from about 5 minutes to about 2 hours at reflux of the inert solvent;
   d) filtering the mixture to produce a solid; and
   e) washing the solid in an inert solvent of the same type used in step (a).

2. The method according to claim 1 wherein the solid is further washed in a solvent selected from the group consisting of methylene chloride and an alcohol having a molecular weight equal to or greater than ethyl alcohol.

3. The method according to claim 2 wherein the inert solvent is selected from the group consisting of hexane, toluene, benzene, chlorobenzene, 2-propanol, 1-2, dichloroethane, and acetonitrile.

4. The method according to claim 3 wherein the silica gel is suitable for human administration.

5. The method according to claim 4 wherein the organophosphorus acid is selected from the group consisting of menthyl-, thymyl-, eugenyl-, vanillyl-, triclosanyl-, and dimenthyl-phosphoric acids.

6. A method for producing phosphorus acid ester derivatives of silicon-hydroxy groups found on the surface of solid silica gel or zeolites comprising the steps of:
   a) creating a suspension of silica gel or zeolites in an inert solvent using an amount of from about 5 ml of inert solvent/g of silica gel or zeolites to about 100 ml of inert solvent/g of silica gel or zeolites, wherein free hydroxy groups are present in the silica gel or zeolites;
   b) treating the suspension with an organophosphorus acid to create a mixture using a ratio of organophosphorus acid molecules to free hydroxy groups in the silica gel or zeolites of from about 0.01:1 to about 100:1;
   c) reacting the mixture for about 1 to about 4 hours at 25° C.;
   d) filtering the mixture to produce a solid; and
   e) washing the solid in an inert solvent of the same type used in step (a).

7. The method according to claim 6 wherein the solid is further washed in a solvent selected from the group consisting of methylene chloride and an alcohol having a molecular weight equal to or greater than ethyl alcohol.

8. The method according to claim 7 wherein the silica gel is suitable for human administration.

9. The method according to claim 8 wherein the organophosphorus acid is selected from the group consisting of menthyl-, thymyl-, eugenyl-, vanillyl-, triclosanyl-, and dimenthyl-phosphoric acids.

10. A method for producing phosphorus acid ester derivatives of silicon-hydroxy groups found on the surface of solid silica gel or zeolites comprising the steps of:
    a) preparing a solution of phosphoric acid anhydride in an alcohol using a ratio of phosphoric acid anhydride to alcohol of from about 1:3 to about 1:300;
    b) creating a suspension of silica gel or zeolites in the solution using an amount of from about 5 ml of solution/g silica gel or zeolites to about 100 ml of solution/g of silica gel or zeolites wherein free hydroxy groups are present in the silica gel or zeolites;
    c) heating the suspension for from about 5 minutes to about 2 hours at reflux;
    d) filtering the mixture to produce a solid; and
    e) washing the solid in an alcohol of the same type used in step (a).

11. The method according to claim 10 wherein the solution further comprises an inert solvent.

* * * * *